(12) United States Patent
Sugimoto et al.

(10) Patent No.: US 6,320,401 B1
(45) Date of Patent: Nov. 20, 2001

(54) SUBSTRATE INSPECTION USING THE PROPAGATION CHARACTERISTICS OF RF ELECTROMAGNETIC WAVES

(75) Inventors: Yoshimi Sugimoto; Yoshikazu Nakayama; Masao Watanabe, all of Tokyo (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 09/327,672

(22) Filed: Jun. 8, 1999

(30) Foreign Application Priority Data

Jun. 15, 1998 (JP) .................................................. 10-167024
Jul. 7, 1998 (JP) .................................................. 10-191489

(51) Int. Cl.[7] ............................ G01N 22/02; G01R 31/26
(52) U.S. Cl. ............................ 324/765; 324/537; 324/639
(58) Field of Search .................................... 324/512, 520, 324/527, 537, 637, 638, 639, 765

(56) References Cited

U.S. PATENT DOCUMENTS

| | | | | |
|---|---|---|---|---|
| 3,715,667 | * | 2/1973 | Nicolson | 324/637 |
| 4,634,963 | * | 1/1987 | Lunden | 324/632 |
| 5,424,633 | * | 6/1995 | Soiferman | 324/158.1 |

OTHER PUBLICATIONS

Tanroku Miyoshi, et al. "Analysis of Microwave Planar Circuit," Transactions of the IEICE (Institute of Electronics, Information and Communication), vol. 55–B, 1972, pp. 441–448 (Month Unavailable).

Philip M. Morse, et al. "Method of Theoretical Physics, Part II," McGraw–Hill, 1953, pp. 1360–1393 (Month Unavailable).

* cited by examiner

*Primary Examiner*—Glenn W. Brown
(74) *Attorney, Agent, or Firm*—Oblon, Spivak, McClelland, Maier & Neustadt, P.C.

(57) ABSTRACT

A substrate inspection device successively stacks a first electrode plate, a standard substrate, a second electrode plate, a sample substrate, and a third electrode plate, in that order, with the sample substrate and the standard substrate placed in symmetrical opposition. A network analyzer both measures the propagation characteristics of RF electromagnetic waves from the second electrode plate to the first electrode plate as standard characteristics and measures the propagation characteristics of RF electromagnetic waves from the second electrode plate to the third electrode plate as the test characteristics. The quality of the sample substrate can be determined by comparing the measured standard characteristics with the test characteristics, thereby enabling, for example, the simple detection of defects inside a multilayer sample substrate.

21 Claims, 5 Drawing Sheets

SUBSTRATE INSPECTION USING THE PROPAGATION CHARACTERISTICS OF RF ELECTROMAGNETIC WAVES

BACKGROUND OF THE INVENTION

1. Field of the Invention

The present invention relates to a method and device for the inspection of a substrate, and more particularly to the method and device for the inspection of defects inside a substrate and the inspection of contamination of the surface of a substrate.

2. Description of the Related Art

The current demand for improvements in the productivity and degree of integration of integrated circuits has resulted in a trend to both expanding the diameter of silicon wafers, which are single-layer substrates on which integrated circuits are formed, from the 200 mm of the prior art to 300 mm and reducing the width of lines making up the integrated circuits to the order of approximately 0.25 $\mu$m.

The presence of defects such as foreign matters or contamination on the surface of the above-described large-diameter silicon wafers, however, has a serious effect when forming a large number of extremely compact integrated circuits. A silicon wafer on which integrated circuits are to be formed must therefore be examined as a sample substrate to discover defects on the surface and carry out corrections or countermeasures.

Methods for inspecting for defects on the surface of a sample substrate such as a silicon wafer include light scattering, SEM/EPMA (Scanning Electron Microscope/Electron Probe Microanalysis), and SEM/AES (SEM/Auger Electron Spectroscopy).

The surface of a sample substrate can be inspected for defects in any of the abovementioned methods of the prior art, but in each case, the construction of the apparatus is complex and of a large scale. In addition, analysis by these methods is complicated and time-consuming, and the addition of a substrate inspecting device to a circuit fabrication line to allow, for example, automatic inspection of sample substrates, has proven to be extremely difficult.

At present, multilayer substrates such as PWB (Printed Wiring Boards) are being used to form complex circuits at high density. A typical multilayer substrate is a circuit substrate in which films or layers of various materials such as copper, polyamide, glass, and epoxy are stacked as a single unit and through-holes are formed to allow conduction between the different layers.

Defects such as minute foreign matters or faults in wiring may easily occur when fabricating this type of multilayer substrate because many processes are used to form the microscopic structures. For example, particles of material that are produced in processes involving cutting or grinding may easily adhere to the processed surface as foreign matters, and mask material such as photoresist in photo-etching processes also tends to remain on the surface.

These types of defects are difficult to completely eliminate despite cleaning of the surface after each process to prevent such defects. The sampling inspection of completed multilayer substrates to detect defects and analyze the causes of defects is crucial for raising yield, but defects may also easily occur inside the substrate because multilayer substrates are formed by successively stacking a large number of layers and films, and the inspection of defects in the interior of a completed multilayer substrate is difficult.

When inspecting for the presence of defects in this type of multilayer substrate, wires are conventionally connected to the many terminals of the completed multilayer substrate and current is actually conducted to each part of the multilayer substrate. When the existence of a defect is determined in this inspection, the location of the defect is determined, the multilayer substrate is cut, and when the defect is found, the material and construction are analyzed. In the above-described method of inspecting a substrate, wires must be connected to the many terminals of the completed multilayer substrate to actually conduct electricity to each part. Moreover, once a defect that has been determined to exist, the position must then be determined, and the multilayer substrate must be cut repeatedly until the defect is actually found.

The prior-art method of inspecting a substrate therefore entails the demanding tasks of first determining whether a defect exists inside a multilayer substrate and then determining the position of the defect. As a result, the method of the prior art requires considerable time and is difficult to automate.

SUMMARY OF THE INVENTION

It is an object according to the present invention to provide a method and device that can easily determine whether or not a defect is present inside a substrate and that can easily determine the position of a defect.

It is an another object according to this invention to provide a method and device that can easily determine whether or not a defect exists on the surface of a sample substrate and that allows analysis of the distribution and composition of a defect.

One substrate inspection device according to this invention includes a standard substrate, a first electrode plate, a second electrode plate, a third electrode plate, a network analyzer, and a quality judging means.

In the substrate inspection device of this invention, the presence of defects in a sample substrate, which is the object of inspection, can be easily determined without connecting wiring to the many terminals of the sample substrate and actually conducting electricity to each part, by: arranging the first electrode plate, the standard substrate, the second electrode plate, the sample substrate, and the third electrode plate, in that order, with the standard substrate and sample substrate symmetrically opposed to each other; using a network analyzer to both measure the propagation characteristics of RF (Radio Frequency) electromagnetic waves from the second electrode plate to the first electrode plate as the standard characteristics and measure the propagation characteristics of RF electromagnetic waves from the second electrode plate to the third electrode plate as the test characteristics; and then comparing the test characteristics with the measured standard characteristics to determine whether the sample substrate is good or bad.

For example, the presence of a defect inside a sample substrate will cause RF electromagnetic waves to scatter, and the presence of the defect is determined because the measurement results of these propagation characteristics by the network analyzer will therefore differ from the results for the standard substrate. In this case, the network analyzer need only be connected in advance to the first to third electrode plates, and there is no need to connect wires to the many terminals of the sample substrate that is to be inspected and actually conduct electricity to each part.

In the case of arranging the first electrode plate, the standard substrate, the second electrode plate, the sample substrate, and the third electrode plate in that order, these components may be placed in contact and stacked, or they may be positioned out of contact with minute gaps between each component. Placing the components in contact simplifies the arrangement and results in good propagation of the electromagnetic waves, but positioning the components out of contact can prevent contamination of the sample substrate. The type of arrangement should be selected according to necessity.

In the substrate inspection device of this invention, the central portion of the second electrode plate where the standard substrate and sample substrate are positioned may be formed in a reticulated form and the outer edge portion of the second electrode plate to be connected to the network analyzer may be divided into a plurality of portions, and the network analyzer may both apply RF electromagnetic waves to one of the plurality of outer edge portions of the second electrode plate and measure the RF electromagnetic waves generated at at least one of the plurality of outer edge portions.

In this case, the measurement results by the network analyzer will differ for a case in which a defect exists in the sample substrate between the position of the plurality of outer edge portions of the second electrode plate at which RF electromagnetic waves are applied and the position at which a measurement is taken and a case in which a defect does not exist.

The position of defects in the sample substrate therefore can be determined from the measurement results by the network analyzer by fixing the input position of RF electromagnetic waves while sequentially switching the output position, by fixing the output position while sequentially switching the input position, by rotating the standard substrate and sample substrate with respect to the second electrode plate, or by a combination of these methods.

As an actual method of determining the position of defects of a sample substrate, one outer edge portion of the second electrode plate at which the network analyzer measures RF electromagnetic waves can be sequentially switched and the distribution of defects of the sample substrate can be analyzed as positions relative to the second electrode plate based on the measurement results by the network analyzer. In this case, the positions of defects in the sample substrate can be effectively determined and this determination does not necessitate moving each substrate or electrode plate.

In the substrate inspection device of this invention, the one outer edge portion of the second electrode plate at which the network analyzer applies RF electromagnetic waves can be sequentially switched and the distribution of defects of the sample substrate can be analyzed as positions relative to the second electrode plate based on the measurement results by the network analyzer. In this case, the position of defects in the sample substrate can be effectively determined, and this determination does not necessitate moving each substrate or electrode plate.

In the substrate inspection device of this invention, the standard substrate and sample substrate can be rotated relative to the second electrode plate, and the distribution of defects of the sample substrate can be analyzed as positions relative to the second electrode plate based on the measurement results by the network analyzer. In this case, the position of defects in the sample substrate can be determined with good accuracy.

In the substrate inspection device of this invention, the following relations:

$a \approx \lambda$ $d \ll \lambda$ may be satisfied where $\lambda$ is the wavelength of RF electromagnetic waves generated by the network analyzer, d is the thickness of the sample substrate and standard substrate, and a is the outer dimension in the planar direction of the sample substrate and standard substrate.

In this case, a planar circuit that propagates RF electromagnetic waves can be formed whereby the position of defects of the sample substrate can be determined by existing arithmetic processes. Another substrate inspection device according to this invention includes a standard substrate, an electrode member, a substrate arranging structure, a network analyzer, and a quality judging means.

In the substrate inspection device of this invention, the substrate arranging structure places the standard substrate and sample substrate in symmetrical opposition, in this state the network analyzer propagates RF electromagnetic waves in the electrode member and measures the characteristics, and the quality judging means determines whether or not defects exist on the surface of the sample substrate based on these measurement results.

Because the state of the surface of the sample substrate can be inspected based on the propagation characteristics of RF electromagnetic waves, the surface state of a sample substrate can be inspected quickly and easily by a device of simple structure and small scale, thereby allowing, for example, the automatic inspection of a silicon wafer as a sample substrate during the process of forming integrated circuits.

The substrate inspection device according to this invention may further include a data storing means in which are registered in advance measurement results by a network analyzer of a pair of standard substrates placed in symmetrical opposition with an interposed electrode member, whereby the quality judging means can determine the presence of defects by comparing the measurement results registered in the data storing means with the measurement results measured from the sample substrate.

In this case, the measurement results by the network analyzer are compared for a state in which a standard substrate is placed in opposition to a standard substrate with an interposed electrode member and a state in which a sample substrate is placed in opposition to a standard substrate. In this case, the two measurement results agree when defects are not present on the surface of the sample substrate, and the two measurement results diverge when defects are present on the surface of the sample substrate. The presence of defects on the surface of a sample substrate can therefore be detected with good accuracy in terms of the results of comparison with the standard substrate.

The electrode member may include a multiplicity of linear electrode lines arranged in parallel each other in a plane form; one output terminal to which either the odd-numbered or even-numbered of the multiplicity of electrode lines are connected in common; and a plurality of input terminals that are each connected to one of a plurality of portions of the other of the odd-numbered and even-numbered of the multiplicity of electrode lines.

In addition, the network analyzer may sequentially supply RF electromagnetic waves to the plurality of input terminals of the electrode member and detect each of the RF electromagnetic waves sequentially generated at the output terminal of the electrode member.

In this case, the distribution of defects of the sample substrate can be detected from the plurality of measurement results of this network analyzer because RF electromagnetic waves are sequentially applied from the network analyzer for each of the plurality of divided sectors of either the odd-numbered or even-numbered of the multiplicity of electrode lines arranged on the electrode member, and the RF electromagnetic waves that are then sequentially generated at the other of the odd-numbered and even-numbered of the multiplicity of electrode lines are individually detected by the network analyzer.

In addition, the quality judging means may also generate a scattering matrix based on the plurality of RF electromagnetic waves that are sequentially detected by the network analyzer and then analyze the distribution of defects of the sample substrate from this scattering matrix.

In this case, the distribution of defects of the sample substrate reflected in this scattering matrix can be analyzed effectively because the scattering matrix is generated from the RF electromagnetic waves detected for each of the plurality of sectors of the multiplicity of electrode lines of the electrode member.

The substrate inspection device according to this invention may also include relative rotating means for rotating the standard substrate and sample substrate relative to the electrode member; the substrate arranging structure may place the standard substrate and sample substrate in opposition to each other and out of contact with and separated by a predetermined distance from the interposed electrode member; and the quality judging means may analyze the distribution of defects of the sample substrate based on the plurality of measurement results by the network analyzer that correspond to the rotation of the relative rotating means.

In this case, the standard substrate and sample substrate are placed by the substrate arranging structure in opposition to each other, out of contact with and separated by a predetermined distance from the interposed electrode member, and the standard substrate and sample substrate are rotated relative to the electrode member by the relative rotating means. The distribution of defects of the sample substrate can be analyzed with good accuracy because the distribution of defects of the sample substrate are analyzed by the quality judging means based on the plurality of measurement results by the network analyzer that correspond to this rotation.

The substrate inspection device according to this invention may further include a surface charging structure for charging the surfaces of the standard substrate and sample substrate that confront the electrode member.

In this case, the surfaces of the standard substrate and sample substrate that confront the electrode member are charged by the surface charging structure, and foreign matters adhering to the surface of the sample substrate is therefore charged in accordance with its composition. The propagation characteristics of the RF electromagnetic waves of the electrode member are changed by this charging of foreign matters on the surface of the sample substrate, and the presence or distribution of foreign matters on the surface of the sample substrate can therefore be detected effectively based on the measurement results of the RF electromagnetic waves.

In the substrate inspection device of this invention, the substrate arranging structure may place the standard substrate and sample substrate in opposition to each other, and out of contact with and separated by a predetermined distance from the interposed electrode member; and the surface charging structure may supply ionized air to the surfaces of the standard substrate and sample substrate that confront the electrode member.

In this case, the standard substrate and sample substrate are placed by the substrate arranging structure in opposition to each other, out of contact with and separated by a predetermined distance from the interposed electrode member; and the surfaces of the standard substrate and sample substrate that confront the electrode member are supplied with ionized air by the surface charging structure.

The surfaces of the standard substrate and sample substrate can accordingly be charged without contacting the electrode, and the surface of the sample substrate can be charged without contaminating the surface.

In the substrate inspection device of this invention, moreover, the electrode member may include a multiplicity of linear electrode lines arranged in parallel each other in a plane form, and the surface charging structure may supply ionized air to the gaps between the multiplicity of electrode lines of the electrode member.

In this case, ionized air is supplied by the surface charging structure to the gaps between the multiplicity of linear electrode lines arranged in parallel in plane of the electrode member, and ionized air therefore can be reliably and simply supplied even when only a small gap exists between the standard substrate and sample substrate.

In the substrate inspection device of this invention, the surface charging structure can freely vary the state of ionization of air supplied to the surfaces of the standard substrate and sample substrate, and the quality judging means can analyze the composition of foreign matters existing on the surface of the sample substrate based on changes in the measurement results by the network analyzer that correspond to the state of ionization of the air. In this case, the state of ionization of air that the surface charging structure supplies to the surfaces of the standard substrate and sample substrate varies, the charged state of foreign matters existing on the surface of the sample substrate changes, and the measurement results by the network analyzer correspondingly change, and the composition of foreign matters present on the surface of the sample substrate therefore can be easily analyzed by the quality judging means based on these changes. The substrate inspection device according to this invention may further include a dryness maintaining structure for keeping dry at least the atmosphere in which the standard substrate, the electrode member, and the sample substrate are located.

In this case, the atmosphere in which at least the standard substrate, the electrode member, and the sample substrate are located is kept in a dry state by the dryness maintaining structure. This provision prevents natural discharge of the surface of the sample substrate and adequately maintains the charged state, whereby changes in the state of the surface of the sample substrate can be prevented and the accuracy of inspection can be improved.

The substrate inspection device according to this invention may further include an electromagnetic shielding structure for cutting off the intrusion of electromagnetic waves to the locations of the standard substrate, the electrode member, and the sample substrate.

In this case, the intrusion of electromagnetic waves to the locations of the standard substrate, the electrode member, and the sample substrate is cut off by the electromagnetic shielding structure, thereby preventing the intrusion of electromagnetic waves from the outside as noise to electrode member that propagates RF electromagnetic waves and enabling surface inspection of the sample substrate to be carried out with good accuracy.

Each of the various means described in this invention may be formed as necessary to realize their functions, and, for example, may be dedicated hardware that realizes the predetermined function, a computer endowed with the predetermined function by a program, a predetermined function realized inside a computer by a program, or a combination of these forms.

In addition, the outer dimensions described in this invention indicate the size of the outer circumference of a substrate, i.e., the diameter when the substrate is in disk form, and the length of one side when the substrate is a square.

The above and other objects, features, and advantages according to the present invention will become apparent from the following description with reference to the accompanying drawings which illustrate examples of the present invention.

BRIEF DESCRIPTION OF THE DRAWINGS

A more complete appreciation of the invention and many of the attendant advantages thereof will be readily obtained as the same becomes better understood by reference to the following detailed descriptions when considered in connection with the accompanying drawings, wherein.

DETAILED DESCRIPTION OF THE PREFERRED EMBODIMENTS

Referring now to the drawings, wherein like reference numerals designate identical or corresponding parts throughout the several views, and more particularly to FIGS. 1–6b thereof, there are illustrated exemplary embodiments of the present invention.

The first embodiment of the invention is next described with reference to FIG. 1 and FIG. 2.

Figure 1:
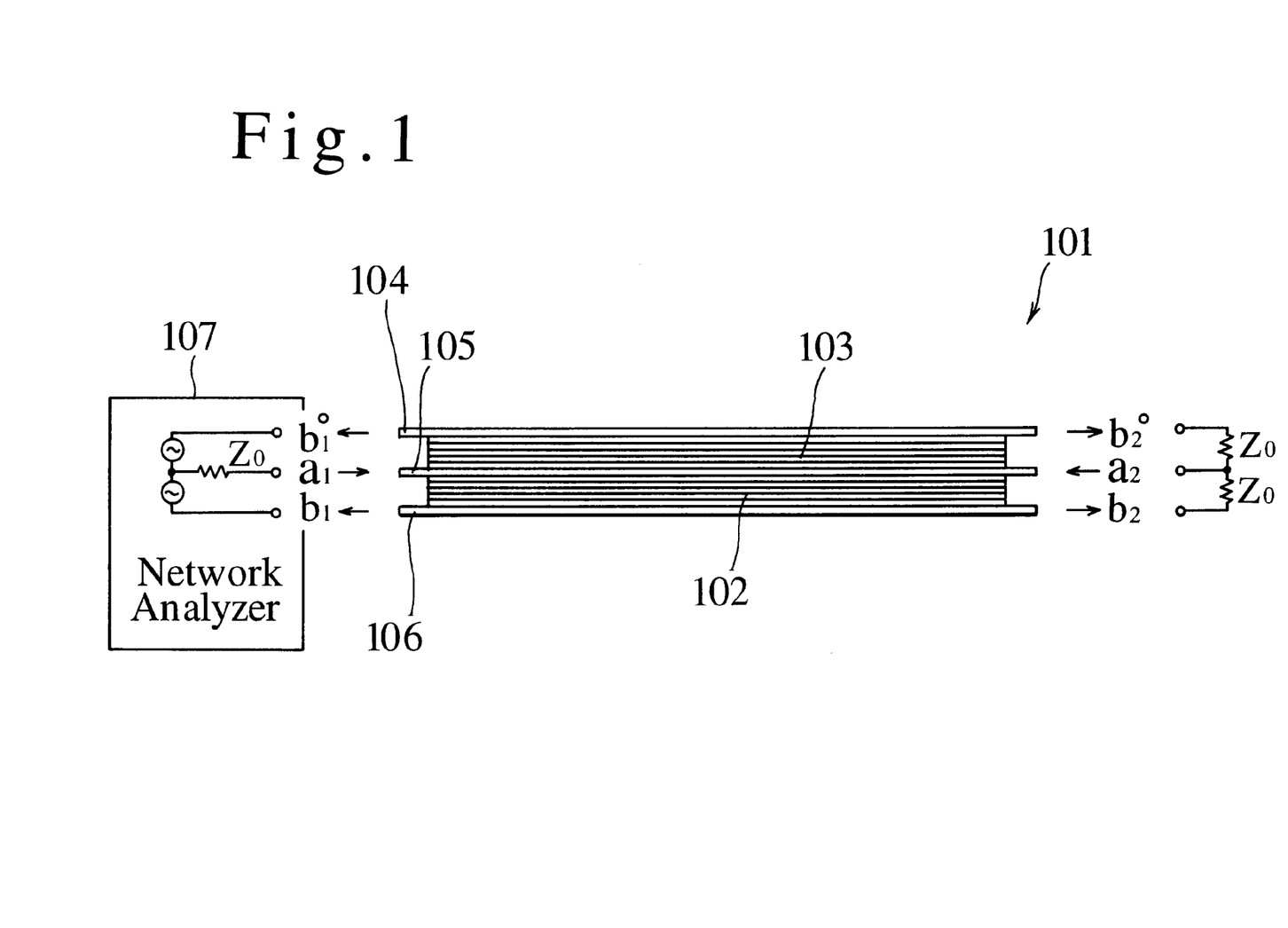
FIG. 1 is a schematic view showing the substrate inspection device according to the first embodiment of the invention.

Referring to FIG. 1, in substrate inspection device 101 of this embodiment, the structure of sample substrate 102 that is the multilayer substrate to be inspected is specified in advance, and standard substrate 103 is prepared in advance as a clean, non-defective multilayer substrate of symmetrical construction to that of the sample substrate. In addition, there are first to third electrode plates 104–106, and these electrode plates 104–106 are connected to one network analyzer 107.

Each of substrates 102 and 103 are formed in a disk shape having a thickness d of about 5 mm and a diameter a, which is the outer dimension, of 40 cm. The central portions of first and third electrode plates 104 and 106 are composed of metallic disks of approximately the same shape as substrates 102 and 103, and these are supported by a rectangular resin outer frame.

Figure 2:
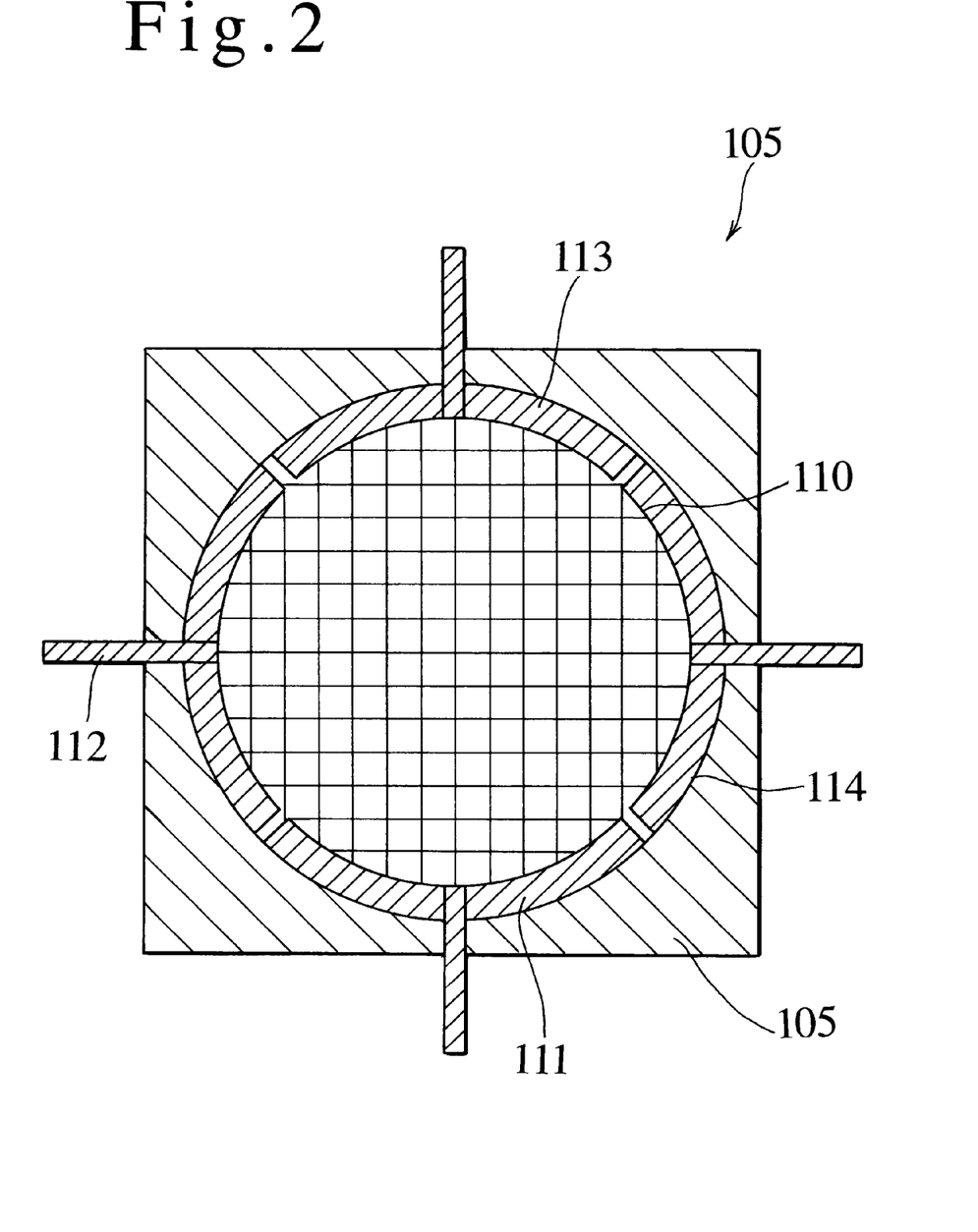
FIG. 2 is a plan view showing the second electrode plate.

However, as shown in FIG. 2, central portion 110 of second electrode plate 105 has approximately the same disk shape as substrates 102 and 103 but is formed in a reticulate form, and four connection terminals 111–114 that are each connected to network analyzer 107 are formed on the outer edge portion of second electrode plate 105.

To explain in greater detail, central portion 110 of second electrode plate 105 is formed in the same disk shape as substrates 102 and 103, has a reticulated form with each interstice being approximately 10×10 mm square, and is composed of thin lines of gold 0.5 mm in diameter. Connection terminals 111–114 formed on the outer edge portion of this central portion 110 are each formed as quarter arcs and are all supported by a single rectangular resin frame 115.

The reticulated structure of central portion 110 of second electrode plate 105 minimizes the surface area of the portion that actually functions as an electrode. As a result, the effects of contamination, adherence of foreign matters, or the roughness of the surface are all reduced, thereby preventing changes over time or changes in conditions during measurement. Moreover, the "skin depth" of RF electromagnetic waves is made substantially uniform and the effect of scattering of RF electromagnetic waves on the electrode surface is reduced and stabilized.

In substrate inspection device 101 of this embodiment, network analyzer 107 is set to generate RF electromagnetic waves of wavelength $\lambda$ of approximately 20–50 cm that satisfy the relation:

$a \approx \lambda$ $d \ll \lambda$ where d is the plate thickness of sample substrate 102 and standard substrate 103; and a is the diameter, which is the outer dimension in the planar direction, of sample substrate 102 and standard substrate 103. A personal computer (not shown) is connected to this network analyzer 7, and this personal computer includes as hardware a CPU (Central Processing Unit), ROM (Read Only Memory), RAM (Random Access Memory), and an I/F (Interface).

A predetermined program is installed beforehand as software in ROM or RAM, and an operation control function, quality judging function, connection switching function, and distribution analyzing function are realized by the personal computer through the execution by the CPU of various processes in accordance with the program.

The operation control function of the personal computer corresponds to operation control by the CPU of network analyzer 107 connected to the I/F in accordance with the program installed in memory, whereby network analyzer 107 is caused to execute the measurement operations of the quality judging mode and position judging mode.

To describe this in more detail, under the settings of quality judging mode and with standard substrate 103 and sample substrate 102 placed in symmetrical opposition and first electrode plate 104, standard substrate 103, second electrode plate 105, sample substrate 102, and third electrode plate 106 arranged in succession, network analyzer 107 is caused to measure the propagation characteristics of RF electromagnetic waves from second electrode plate 105 to first electrode plate 104 as the standard characteristics and the propagation characteristics of RF electromagnetic waves from second electrode plate 105 to third electrode plate 106 as the test characteristics.

The quality judging function corresponds to arithmetic processing by the CPU of the output data of network analyzer 107 that are received from the outside from I/F in accordance with a program installed in memory, whereby the standard characteristics and the test characteristics measured by network analyzer 107 are compared and the quality of sample substrate 102 is determined according to whether these data match or not.

If, as the judgment result, sample substrate 102 is determined to be defective, the operation control of the position judging mode is carried out by the previously described operation control function. In this case, network analyzer 107 is caused to apply RF electromagnetic waves to one of the four connection terminals 111–114 of second electrode plate 105 and measure the RF electromagnetic waves generated at another of the four connection terminals 111–114.

In the connection switching function, in the above-described state, network analyzer 107 successively switches one of connection terminals 111–114 of second electrode plate 105 that measures RF electromagnetic waves, and every time this switching is completed, network analyzer 107 successively switches one of the four connection terminals 111–114 of second electrode plate 105 to which RF electromagnetic waves are applied.

In the distribution analyzing function, the distribution of defects in sample substrate 102 is analyzed as the relative position with respect to second electrode plate 105 based on the 12 (=4×3) measurement results by network analyzer 107 according to the abovementioned switching operation. In this embodiment, the planar circuit that propagates RF electromagnetic waves according to the above-described relations "a≈λ" and "d<<λ" is formed as a constant circuit of two-dimensional distribution, and the position of defects is determined by known arithmetic processing using this circuit.

In substrate inspection device 101 of this embodiment in the above-described construction, first electrode plate 104, standard substrate 103, second electrode plate 105, sample substrate 102, and third electrode plate 106 are arranged in order with standard substrate 103 and sample substrate 102 placed in symmetrical opposition.

In this state, network analyzer 107 measures the propagation characteristics of RF electromagnetic waves from second electrode plate 105 to first electrode plate 104 as the standard characteristics and the propagation characteristics of RF electromagnetic waves from second electrode plate 105 to third electrode plate 106 as the test characteristics. The standard characteristics and test characteristics measured in this way are then compared by the personal computer, and the quality of sample substrate 102 is determined based on whether or not the measured values coincide. For example, if a defect exists in sample substrate 102, RF electromagnetic waves scatter at that point, measurement results of the propagation characteristics by network analyzer 107 diverge from those for standard substrate 103, and the presence of the defect is determined. When the presence of a defect is determined in this way, the process of determining the location of the defect is automatically initiated in substrate inspection device 101 of this embodiment.

In this case, network analyzer 107 both applies RF electromagnetic waves to one of the four connection terminals 111–114 of second electrode plate 105 and measures the RF electromagnetic waves generated at another of connection terminals 111–114, sequentially switching the connection terminal 111–114 at which RF electromagnetic waves are measured.

Three output measurement results are thus obtained for one input, and upon each completion, the terminal of connection terminals 111–114 to which RF electromagnetic waves are applied is also switched. In this way, 12 (=4×3) measurement results by network analyzer 107 are obtained, and the distribution of defects in sample substrate 102 are analyzed as the relative position with respect to second electrode plate 105 based on these measurement results by a known arithmetic process.

In this embodiment, a planar circuit that propagates RF electromagnetic waves is formed as a constant circuit of two-dimensional distribution, and the propagation of RF electromagnetic waves on this type of planar circuit is described by a two-dimensional Helmholtz equation when a sine wave of frequency ω is applied. In other words, if the direction of the x/y axes is assumed to be parallel to the faces of substrates 102 and 103, then:

$$(\nabla_2^2 + k^2) V(x, y) = [j\omega/(\delta + j\epsilon\omega)]\rho(x', y') \tag{1}$$

$$k^2 = \epsilon\mu\omega^2 - j\mu\delta\omega \tag{2}$$

$$\nabla_2^2 = (\partial^2/\partial x^2) + (\partial^2/\partial y^2) \tag{3}$$

$$k = 2\pi/\lambda \tag{4}$$

V(x, y) represents the potential of first and third electrode plates 104 and 106 with respect to second electrode plate 105, and are a function of planar coordinates (x, y) that satisfies the relation V(x, y)=dEz(x, y). The right side of equation (1) represents the scattering effect of electromagnetic waves by the charge distribution ρ(x', y') of a defect. A defect can be measured theoretically by equations (1)–(4) because the dielectric constant E and permeability μ of sample substrate 102 change due to the presence of a defect, but this change can be expected to be minute. Organic contaminants or inorganic particles on the wafer surface are prone to charging at low humidity, and the effect of the right side of equation (1) is therefore great when these types of defects are present on sample substrate 102. The solution to equation (1) is resolved, and if the solution is $V_0$ when there is no electric charge (electromagnetic wave propagation within a uniform field), then:

$$(\nabla_2^2 + k^2) V_0(x, y) = 0 \tag{5}$$

Using this $V_0$, the abovementioned equation (1) becomes:

$$V(x, y) = V_0(x, y) + \iint G(x, y|x', y') \rho(x', y') dx'dy' \tag{6}$$

$$G(x, y|x', y') = \ln\{1/\sqrt{(x-x')^2 + (y-y')^2}\} \tag{7}$$

The solution of a Helmholtz equation when electromagnetic waves are propagated within a uniform field is explained in detail by Ogoe and Miyoshi in "Transactions of the IEICE (Institute of Electronics, Information and Communication)" (Vol. 55-B, 1972. p. 441, in Japanese) and in *Methods of Theoretical Physics*, Part II (Morse, Philip M. and Feshback, Herman. *Methods of Theoretical Physics*, Part II . McGraw-Hill, 1953. p. 1361).

The circuit network constant can be calculated as a function of the distribution of defects by the above-described equation (7). For example, the resonance frequency of sample substrate 102 is proportional to $(\epsilon\mu)^{-\frac{1}{2}}$, and the resonance frequency (point) is therefore expanded when the dielectric constant ε of sample substrate 102 is distributed by the distribution of defects. In addition, the two-dimensional distribution of capacitance C can be expected to be observed from the distribution of defects because the capacitance C of sample substrate 102 is directly proportional to the dielectric constant ε. Change in inductance L, however, can be expected to be minute despite the distribution of defects because the inductance L of sample substrate 102 is proportional to permeability μ.

In substrate inspection device 101 of this embodiment, network analyzer 107 applies RF electromagnetic wave $a_1$ to one of the four connection terminals 111–114 of second electrode plate 105 and measures RF electromagnetic wave $a_2$ generated at another of connection terminals 111–114 and RF electromagnetic waves $b_1^0$, $b_2^0$, $b_1$, and $b_2$ generated at first and third electrode plates 104 and 106, as shown in FIG. 1. Scattering parameters "$S_{11}^0$, $S_{12}^0$, $S_{21}^0$, $S_{22}^0$" and "$S_{11}$, $S_{12}$, $S_{21}$, and $S_{22}$" can be calculated from the results of these measurements:

$$\begin{pmatrix} b_1^0 \\ b_2^0 \end{pmatrix} = \begin{pmatrix} S_{11}^0 & S_{12}^0 \\ S_{21}^0 & S_{22}^0 \end{pmatrix} \begin{pmatrix} a_1 \\ a_2 \end{pmatrix} \quad (8)$$

$$\begin{pmatrix} b_1 \\ b_2 \end{pmatrix} = \begin{pmatrix} S_{11} & S_{12} \\ S_{21} & S_{22} \end{pmatrix} \begin{pmatrix} a_1 \\ a_2 \end{pmatrix} \quad (9)$$

The dielectric constant, phase change, and resonance frequency can be calculated from these scattering parameters, and because the distribution of defects is well reflected by the dielectric constant and resonance frequency as described hereinabove, the positions of defects present in sample substrate 102 can be effectively determined if the dielectric constant or resonance frequency is observed by sequentially switching the terminal of connection terminals 111–114 to which RF electromagnetic waves are applied or the one terminal at which RF electromagnetic waves are measured.

Even when the positions of defects of sample substrate 102 are determined in this way, the internal structure of sample substrate 102 is complex and the measurement results by network analyzer 107 are not uniform, and as a result, the positions of defects are determined in substrate inspection device 101 of this embodiment based on the results of comparison with the measurement results of standard substrate 103.

In substrate inspection device 101 of this embodiment, both the presence of defects inside sample substrate 102 and the positions of these defects can be determined by using network analyzer 107 as described hereinabove to compare the RF electromagnetic wave propagation characteristics of sample substrate 102 and standard substrate 103, which are multilayer substrates.

In this case, the burden of this task is lightened and the time reduced because there is no need to connect wiring and actually conduct electricity to the multiplicity of terminals of sample substrate 102, which is the object of inspection. Moreover, the positions of defects can be determined without cutting sample substrate 102, and the work of actually cutting sample substrate 102 and discovering the defects can also be carried out quickly.

In addition, central portion 110 of second electrode plate 105 is formed in a reticulated pattern, thereby mitigating contamination by the portion that actually functions as an electrode. The "skin depth" of RF electromagnetic waves is also made substantially uniform, thereby reducing the scattering effect on the electrode surface and allowing inspection of sample substrate 102 to be carried out stably.

In the above-described embodiment, it is assumed that the first to third electrode plates 104–106, standard substrate 103, and sample substrate 102 are formed separately and then combined in a manual operation.

In substrate inspection device 101 of the abovementioned embodiment, however, there is no need to connect wiring to the multiplicity of terminals and actually conduct electricity to each portion as described hereinabove, and a mechanism that automatically extracts sample substrate 102 from the fabrication line, assembles as described hereinabove, and carries out the work automatically may be realized by a robot arm.

Although an example was described in the above-described embodiment in which second electrode plate 105 is provided with four connection terminals 111–114 and switching is carried out in order, the number of connection terminals can be freely set to any number. Increasing the number of connection terminals of second electrode plate 105 improves the resolution of determining the position of defects but makes the construction of second electrode plate 105 more complex and complicates the connections with network analyzer 7.

On the other hand, decreasing the number of connection terminals of second electrode plate 105 lowers the resolution of determining the position of defects but simplifies the construction of second electrode plate 105 and eases the task of connecting with network analyzer 7. The number of connection terminals should be decided with due consideration given to such conditions as required performance. In the above-described embodiment, an example was described in which the positions of defects in sample substrate 102 are determined by switching the position of applying RF electromagnetic waves and the position of measuring RF electromagnetic waves in second electrode plate 105, but the position of defects may also be determined by, for example, rotating standard substrate 103 and sample substrate 102 relative to second electrode plate 105.

To realize a device (not shown) for automatically carrying out this type of substrate inspection, a relative rotating means may, for example, be formed as a structure that rotates only second electrode plate 105 while fixedly holding first electrode plate 104, standard substrate 103, sample substrate 102, and third electrode plate 106.

A method for rotating second electrode plate 105 relative to each of substrates 102 and 103 may also be combined with a method for switching the positions in second electrode plate 105 of input and measurement of RF electromagnetic waves as described hereinabove, and although the construction in such a case is complex, the accuracy of determining defect locations can be improved.

Figure 3:
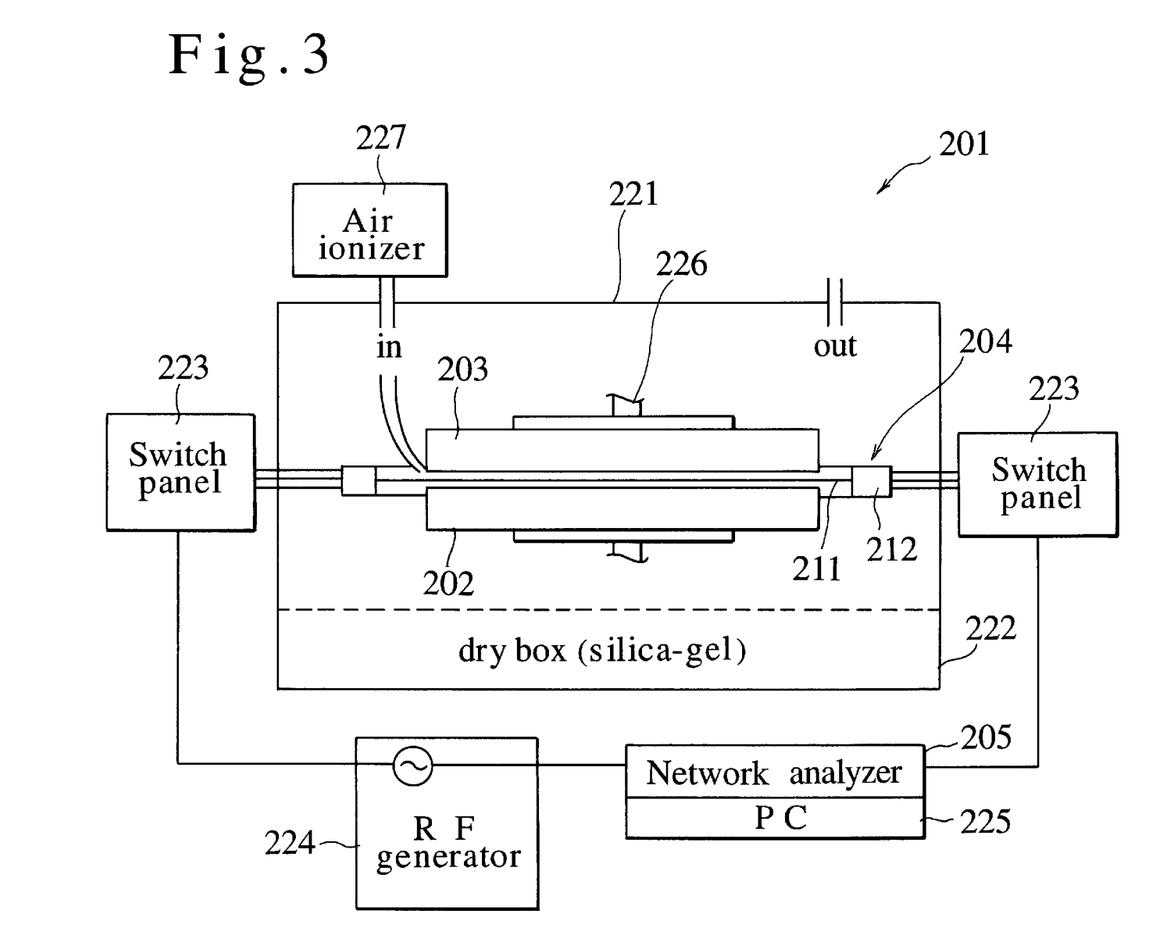
FIG. 3 is a schematic view showing the substrate inspection device according to the second embodiment of the invention.
Figure 4A:
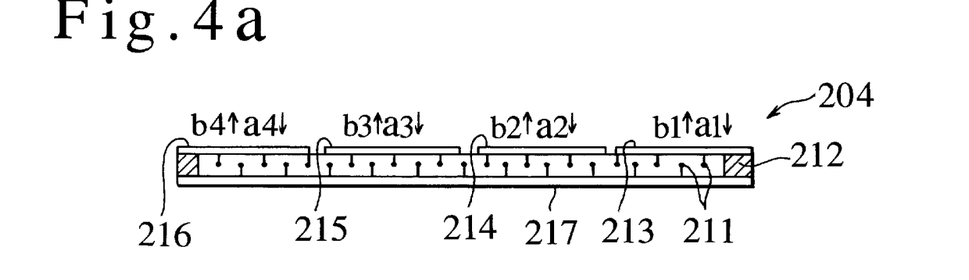
FIG. 4a is a sectional view taken along line A—A in FIG. 4b showing the electrode member.

The second embodiment of the invention is next described with reference to FIG. 3 and FIG. 4. To simplify the explanation in this embodiment, the up and down directions in FIG. 3 are referred to as the up and down directions of the device, the left and right directions are the front and rear, and the directions passing through the plane of the figure are the left and right directions of the device. Accordingly, the front and rear directions of the device are the directions that pass through the plane of figure in FIG. 4a, and the up and down directions in the plane of FIG. 4b. These various directions are expediently defined in the interest of simplifying the description and in no way restrict the directions of the actual device during use or manufacture.

Referring to FIG. 3, substrate inspection device 201 of this embodiment is incorporated in a circuit fabrication line (not shown) for forming integrated circuits on the surface of silicon wafers of disk shape, and a silicon wafer in the process of having integrated circuits fabricated is taken as sample substrate 202. Accordingly, the structure of sample substrate 202 is specified beforehand, and a clean, non-defective standard substrate 203 of symmetrical structure to this sample substrate 202 is been prepared in advance.

Substrate inspection device 201 also includes a single flat electrode member 204 having obverse and reverse sides, and network analyzer 205 is connected to this electrode member 204. As shown in FIG. 4, electrode member 204 includes a multiplicity of linear electrode wires 211 composed of gold approximately 0.1 mm in diameter, and this multiplicity of electrode wires 211 are arranged in parallel in a flat plane.

Figure 4B:
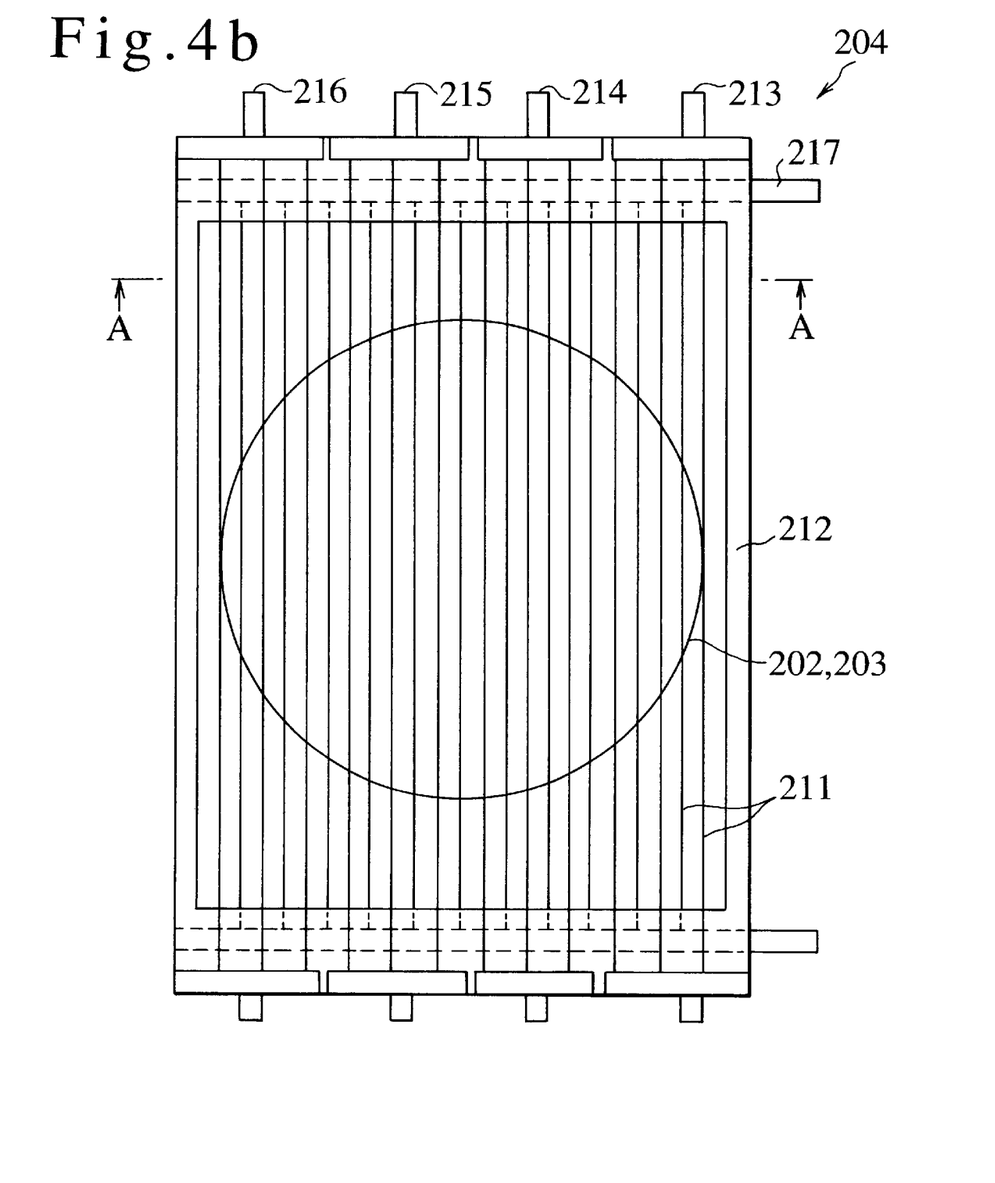
FIG. 4b is a plan view showing the electrode member.

In other words, electrode member 204 includes electrode panel 212 in the form of a rectangular plane as shown in FIG. 4b, and a multiplicity of electrode wires 211 are stretched from the front end to the rear end of this electrode panel 212. Four input terminals 213–216 are provided in order at both the front and rear ends on the upper surface of this electrode panel 212, and one output terminal 217 is provided at both the front and rear ends on the lower surface.

The multiplicity of electrode wires 211 are arranged in a plane. A predetermined number of the odd-numbered electrode wires are allotted to each of four sectors and these sectors are each connected to a respective one of input terminals 213–216. The even-numbered wires are connected to the single output terminal 217. In the figure, three electrode wires 211 are connected to each of four input terminals 213–216, but in actuality, a larger number of electrode wires 211 are connected.

As shown in FIG. 3, electrode member 204 of the above-mentioned construction is fixed horizontally at the central portion inside aluminum shield box 221, which is an electromagnetic shielding structure, and this shield box 221 shields the location of such components as electrode member 204 from the intrusion of electromagnetic waves from the outside.

Dry box 222, which is a dryness maintenance structure, is provided in the bottom of this shield box 221, and this dry box 222 keeps the interior of shield box 221 dry by means of a silica gel (not shown) that it contains.

Network analyzer 205 and RF generator 224 are connected to terminals 213–217 of electrode member 204 by way of switch panel 223 arranged outside shield box 221, and personal computer 225 is connected to this network analyzer 205.

RF generator 224 actually corresponds to one part of network analyzer 205 and generates RF electromagnetic waves. This RF generator 224 is connected by way of switch panel 223 to the four input terminals 213–216 of electrode member 204, and RF electromagnetic waves generated by RF generator 224 are thus supplied in order to the four input terminals 213–216 by switch panel 223.

When switch panel 223 sequentially connects RF generator 224 to one of the four input terminals 213–216 as described hereinabove, characteristic impedance is connected to the three input terminals 213–216 that are not connected to RF generator 224 to prevent a drop in the detection accuracy of RF electromagnetic waves. Standard substrate 203 confronts the multiplicity of electrode wires 211 of electrode member 204, which is arranged horizontally inside shield box 221 as described hereinabove, from above and separated by a predetermined distance, this standard substrate 203 being axially supported by axial support structure 226 so as to allow free rotation in a horizontal direction.

Substrate inspection device 201 of this embodiment and circuit fabrication line are provided with a substrate conveyance structure (not shown), and this substrate conveyance structure conveys sample substrate 202 from the circuit fabrication line and to the position of axial support structure 226 inside shield box 221, and conveys this sample substrate 202 out to the circuit fabrication line or to an accuracy inspection line (not shown) outside shield box 221.

The above-described axial support structure 226 axially supports sample substrate 202 that has been conveyed inside shield box 221 so as to allow free rotation in the horizontal direction such that sample substrate 202 confronts the multiplicity of electrode wires 211 of electrode member 204 from below while remaining separated from electrode member 204 by a predetermined distance.

Symmetrically structured sample substrate 202 and standard substrate 203 are thus supported in a symmetrical state with the multiplicity of electrode wires 211 of electrode member 204 interposed there between, and sample substrate 202 and standard substrate 203 rotate with respect to electrode member 204 while maintaining this symmetrical state.

Air ionizer 227, which is a surface charging structure, is linked to shield box 221, and this air ionizer 227 electrically charges the surfaces of substrates 202 and 203 that confront electrode member 204 by supplying positively or negatively ionized air to the surfaces of sample substrate 202 and standard substrate 203 that confront electrode member 204.

As described hereinabove, electrode member 204 is made up of a multiplicity of electrode wires 211 stretched in parallel on electrode panel 212, and air ionizer 227 therefore actually supplies ionized air to the gaps between multiplicity of electrode wires 211. In addition, the state of ionization of air from air ionizer 227 is freely variable, and these variations are controlled by personal computer 225.

This personal computer 225 realizes a mode switching function, an operation control function, a data storage function, and a quality judging function by executing various processing in accordance with a program installed beforehand.

The mode switching function of personal computer 225 switches the operating mode of substrate inspection device 201 between a data registering mode and an inspecting mode. The operation control function is in effect for both of these operating modes, but the quality judging mode operates only under the setting of the inspecting mode.

Each of the various actions such as the conveyance in and conveyance out of each of substrates 202 and 203 by substrate conveyance structure, the arrangement and rotation of each of substrates 202 and 203 by axial support structure 226, the supply of ionized air and the changes in the state of ionization of the air by air ionizer 227, the output of RF electromagnetic waves by RF generator 224, and the measurement of characteristics by network analyzer 205, are integrated and controlled by the operation control function.

To describe in more detail, under the setting of the data registering mode, the operation control function causes a separate standard substrate 203 to be conveyed to substrate inspection device 201 by means of the substrate conveyance structure and placed by axial support structure 226 in opposition to with standard substrate 203 with electrode member 204 interposed there between. In this state, the operation control function directs such actions as the supply of ionized air and the changes in the state of ionization of the air by air ionizer 227, the output of RF electromagnetic waves by RF generator 224, and the measurement of characteristics by network analyzer 205.

The data storing function stores the measurement results by network analyzer 205 taken with the pair of standard substrates 203 in a symmetrically opposed state with electrode member 204 interposed under the settings of the data registering mode as described hereinabove.

Under the settings of the inspecting mode, the operation control function causes sample substrate 202 to be conveyed from the circuit fabrication line and into substrate inspection device 201 by the substrate conveyance structure and placed by axial support structure 226 in opposition to standard substrate 203 with electrode member 204 interposed there between. In this state, the operation control function directs such actions as the supply of ionized air and changes in the state of ionization of air by air ionizer 227, the output of RF electromagnetic waves by RF generator 224, and the measurement of characteristics by network analyzer 205.

Under the setting of the inspecting mode, the quality judging function compares the measurement results actually measured from sample substrate 202 by network analyzer 205 with the measurement results registered beforehand by the data storing function and inspects for the presence of defects in the surface of sample substrate 202.

The characteristics measured by network analyzer 205 as described hereinabove are, for example, the characteristics of the transmission or scattering of electromagnetic waves. Network analyzer 205 sequentially supplies RF electromagnetic waves to the four input terminals 213–216 of electrode member 204 and measures each of the RF electromagnetic waves corresponding to this input that are sequentially generated at the one output terminal 217, and the quality judging function of personal computer 225 thus generates one scattering matrix from the four measurement results by network analyzer 205.

When defects of sample substrate 202 are inspected as described hereinabove, each of substrates 202 and 203 are rotated with respect to electrode member 204 by axial support structure 226, which is controlled by the quality judging function, and the distribution of defects of sample substrate 202 are analyzed by the quality judging function based on the measurement results by network analyzer 205 that correspond to this rotation.

Ionized air is supplied to the gaps between electrode member 204 and each of substrates 202 and 203 by air ionizer 227 under the control of the operation control function and the surfaces of each of substrates 202 and 203 that confront electrode member 204 are electrically charged, whereby the defects of sample substrate 202 are inspected by the quality judging function based on the measurement results in this state by network analyzer 205.

The state of ionization of air supplied by air ionizer 227 under the control of the operation control function is then varied, bringing about a change in the state of charging of the surfaces of each of substrates 202 and 203, whereby the composition of foreign matters present on the surface of sample substrate 202 is analyzed by the quality judging function based on the corresponding change in the measurement results by network analyzer 205.

In substrate inspection device 201 of this embodiment, a silicon wafer in the process of forming integrated circuits is taken as sample substrate 202 as described hereinabove, and the state of the surface of this sample substrate 202 is therefore not uniform even if defects are not present on the surface. The measurement results for a pair of standard substrates 203 that are registered in the data storing function are therefore registered together with angle identifier data taken when the pair of standard substrates 203 is rotated with respect to electrode member 204.

In substrate inspection device 201 of this embodiment, the charged state of the surfaces of each of substrates 202 and 203 is changed to detect the composition of defects as described hereinabove, and the measurement results by network analyzer 205 are also registered in the data storing function for a case in which the charged state of a pair of standard substrates 203 is similarly changed.

Each of the functions described hereinabove is realized through the use of various hardware as necessary, but the heart of these functions is realized through the operation of a CPU, which is a computer made up of hardware, in accordance with software stored in an information storage medium such as ROM.

Such software is, for example, stored on an information storage medium such as ROM as a control program for causing, for example, a CPU to execute processing such as: the integrated control of the operations of each component, such as the substrate conveyance structure, axial support structure 226, air ionizer 227, RF generator 224, and network analyzer 205; the determination of the presence of defects by comparing measurement results actually measured from sample substrate 202 by network analyzer 205 under this state of control with measurement results registered beforehand in, for example, RAM ; the analysis of the distribution of detected defects of sample substrate 202; and the analysis of the composition of foreign matters present on the surface of sample substrate 202 based on changes in the measurement results by network analyzer 205.

In the above-described construction of substrate inspection device 201 of this embodiment, a silicon wafer at a predetermined fabrication step in the process of forming integrated circuits on the surface of the silicon wafer by a circuit fabrication line is taken as sample substrate 202 for surface inspection.

In this case, sample substrate 202 is conveyed by a substrate conveyance structure from the circuit fabrication line and to substrate inspection device 201, where it is supported by axial support structure 226 in a position opposed to standard substrate 203 with electrode member 204 interposed there between. In this state, shield box 221 is tightly sealed, whereby the intrusion of electromagnetic waves to the positions of each of substrates 202 and 203 and electrode member 204 is prevented and dry conditions are maintained by dry box 222.

Next, the surfaces of each of substrates 202 and 203 that confront electrode member 204 are supplied with ionized air from air ionizer 227 whereby the surfaces of each of substrates 202 and 203 are similarly charged. In this state, an overall inspecting mode is first set as the operation mode, and the overall surface of sample substrate 202 is inspected.

In this case, RF electromagnetic waves are simultaneously and uniformly supplied from RF generator 224 to the four input terminals 213–216 of electrode member 204, and these RF electromagnetic waves are therefore uniformly supplied to the even-numbered positive electrode wires of the multiplicity of positive electrode wires 211 of electrode member 204. RF electromagnetic waves are hereupon generated at the single output terminal 217 connected to the odd-numbered negative electrode wires of the multiplicity of electrode wires 211, and these RF electromagnetic waves are measured by network analyzer 205.

These measurement results are transmitted to personal computer 225, in which are registered results that were similarly measured beforehand from a pair of standard substrates 203, and the measurement results measured from sample substrate 202 are compared with these measurement results for standard substrates 203 that were registered in advance.

Standard substrate 203 is formed with the same structure as sample substrate 202, and the measurement results by network analyzer 205 reflect the surface state of each of substrates 202 and 203. As a result, defects are not present on the surface of sample substrate 202 if the two sets of measurement results that are compared as described hereinabove agree, but defects exist on the surface of sample substrate 202 if the measurement results do not agree.

In substrate inspection device 201 of this embodiment, sample substrate 202, in which defects are confirmed not to exist as described above, is conveyed out of shield box 221 and to the circuit fabrication line by the substrate conveyance structure, and the next sample substrate 202 is conveyed from the circuit fabrication line and to shield box 221.

If, on the other hand, defects are determined to exist in sample substrate 202 as described above, a partial inspection mode is automatically set as the operation mode and the distribution of defects is detected. In this case, RF electromagnetic waves generated by RF generator 224 are sequentially supplied by switch panel 223 to the four input terminals 213–216 of electrode member 204, and the RF electromagnetic waves generated in the single output terminal 217 are individually measured by network analyzer 205 at timings that correspond to the sequential supply of RF electromagnetic waves to input terminals 213–216. Personal computer 225 then generates scattering parameters from the four measurement results by the network analyzer 205, and by comparing these parameters with the scattering parameters of the pair of standard substrates 203 that were registered beforehand, it can be inferred in which of the four divided regions of electrode member 204 that correspond to the four input terminals 213–216 the defect of sample substrate 202 exists.

At this point, axial support structure 226 rotates each of substrates 202 and 203 exactly 90° with respect to electrode member 204, and the abovementioned inspection operation is similarly executed. After this rotation it is again inferred in which of the four divided regions of electrode member 204 defects of sample substrate 202 exist, and in this way, it can be inferred in which of the sixteen regions into which sample substrate 202 is divided front-rear and left-right defects exist.

In substrate inspection device 201 of this embodiment, a sample substrate 202 for which it is confirmed that defects do not exist as described above is conveyed by substrate conveyance structure from the inside of shield box 221 and to the circuit fabrication line, and the next sample substrate 202 is conveyed from the circuit fabrication line and to shield box 221.

In substrate inspection device 201 of this embodiment, moreover, the work of detecting the composition of these defects is automatically initiated when the distribution of defects present on sample substrate 202 is detected as described above. In this case, the state of ionization of air supplied from air ionizer 227 is varied and the state of charging of the surfaces of each of substrates 202 and 203 accordingly changes. The propagation characteristics of RF electromagnetic waves is then measured by network analyzer 205 for each of these changes in the state of charging.

The state of charging of the surfaces of each of substrates 202 and 203 is reflected in the propagation characteristics of RF electromagnetic waves measured in this way, and the change in charging state of an object's surface into which ions are introduced differs according to its substance. As a result, the composition of foreign matters on the surface of sample substrate 202 is analyzed by personal computer 225 based on the measurement results by network analyzer 205.

A sample substrate 202 for which the distribution and composition of foreign matters has been analyzed in this way is not conveyed from inside of shield box 221 and to the circuit fabrication line by the substrate conveyance structure, but rather, is conveyed to a close inspection line for close examination, following which, for example, it is destroyed or cleaned and returned to the circuit fabrication line.

Next, regarding the basic principles of the surface inspection method in the above-described substrate inspection device 201 of this embodiment, substrates 202 and 203 of symmetrical construction are first placed in symmetrical opposition with electrode member 204 interposed there between, and in this electrode member 204 negative electrode wires 211 to which RF electromagnetic waves are applied and positive electrode wires 211 at which RF electromagnetic waves are detected are alternately arranged in parallel.

Figure 5:
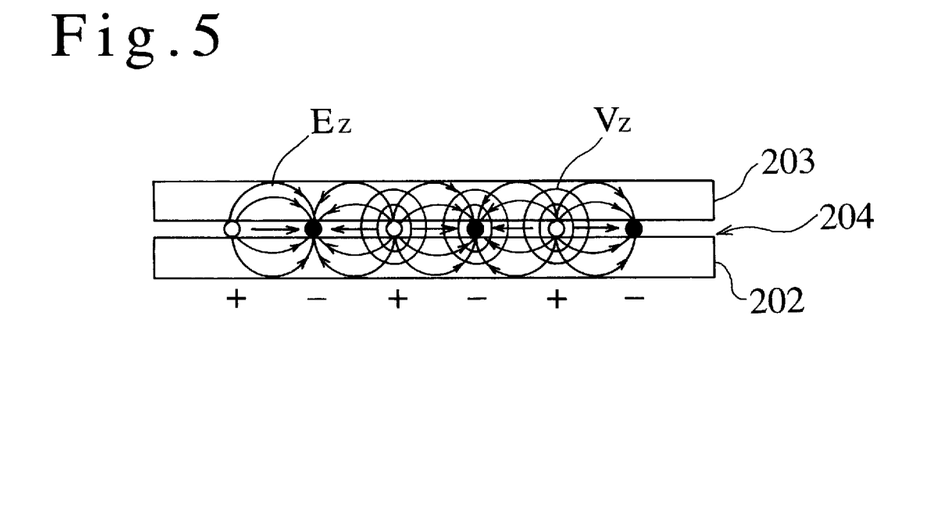
FIG. 5 is a schematic front vertical sectional view showing the state of field and potential generated by propagation of RF electromagnetic waves.

Here, the direction parallel to electrode wires 211 of electrode member 204 is taken as the z direction, the direction in which each of substrates 202 and 203 is positioned with respect to electrode member 204 and which is perpendicular to the z direction is the x direction, and the direction perpendicular to the x and y directions is the y direction. In this case, RF electromagnetic waves are propagated in the z direction, and, as shown in FIG. 5, electric field Ez and potential Vz are formed by positive and negative electrode wires 211.

The propagation state with this type of electric field Ez and potential Vz is described as the relation between dielectric constant $\epsilon$, permeability $\mu$ and conductivity of each of substrates 202 and 203. As is generally known, the electromagnetic waves propagated through the plurality of parallel electrode wires 211 are TEM (Transverse Electromagnetic) waves and are equivalent in nature to plane waves. Electric field Ez is therefore described by a Helmholtz equation as:

$$[(\partial^2/\partial x^2)+(\partial^2/\partial y^2)+k^2]Ez(x, y)=0 \tag{11}$$

$$k^2=\epsilon\mu\omega^2 -j\mu\delta\omega \tag{12}$$

The dielectric constant $\epsilon$ or permeability $\mu$ of sample substrate 202 changes due to the presence of defects, and although defects therefore can be measured theoretically using the above-described equations (11) and (12), these changes can be expected to be minute. Similarly, the scattering matrix generated from sample substrate 202 by itself reflects the presence and distribution of defects, but in actuality, the presence and distribution of defects in sample substrate 202 are difficult to detect from a single scattering matrix.

Figure 6A:
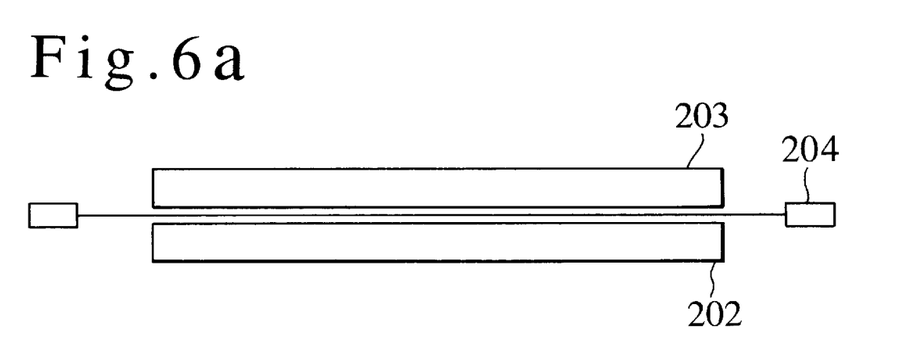
FIG. 6a is a schematic sectional view showing a pair of standard substrates placed in opposition at the obverse side and reverse side of the electrode member.

In substrate inspection device 201 of this embodiment, however, a pair of standard substrates 203 are placed in confrontation with electrode member 204 as shown in FIG. 6a and RF electromagnetic waves are measured in advance, and from the measurement results, the following scattering matrix is generated and registered:

$$\begin{pmatrix} b_1 \\ b_2 \\ b_3 \\ b_4 \end{pmatrix} = \begin{pmatrix} S^0_{11} & S^0_{12} & S^0_{13} & S^0_{14} \\ S^0_{21} & S^0_{22} & S^0_{23} & S^0_{24} \\ S^0_{31} & S^0_{32} & S^0_{33} & S^0_{34} \\ S^0_{41} & S^0_{42} & S^0_{43} & S^0_{44} \end{pmatrix} \begin{pmatrix} a_1 \\ a_2 \\ a_3 \\ a_4 \end{pmatrix} \tag{13}$$

Figure 6B:
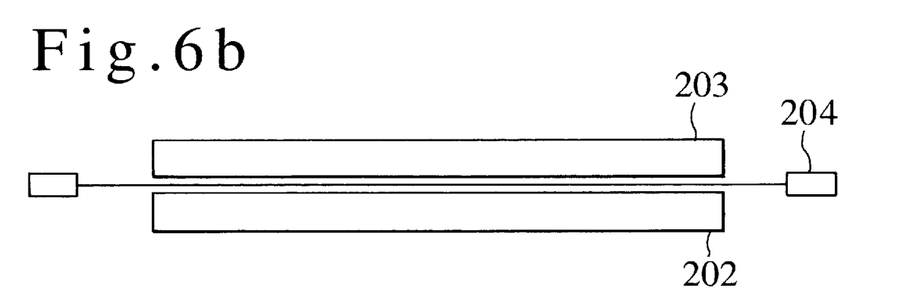
FIG. 6b is a schematic sectional view showing a standard substrate and sample substrate placed in opposition at the obverse side and reverse side of the electrode member.

Then, as shown in FIG. 6b, each of substrates 202 and 203 are placed in confrontation with electrode member 204 and RF electromagnetic waves are measured, and from these measurement results, the following scattering matrix is generated:

$$\begin{pmatrix} b_1 \\ b_2 \\ b_3 \\ b_4 \end{pmatrix} = \begin{pmatrix} S_{11} & S_{12} & S_{13} & S_{14} \\ S_{21} & S_{22} & S_{23} & S_{24} \\ S_{31} & S_{32} & S_{33} & S_{34} \\ S_{41} & S_{42} & S_{43} & S_{44} \end{pmatrix} \begin{pmatrix} a_1 \\ a_2 \\ a_3 \\ a_4 \end{pmatrix} \tag{14}$$

The scattering matrix actually measured from each of substrates 202 and 203 in this way is then compared with the registered scattering matrix, whereby the presence of defects in sample substrate 202 can be determined with good accuracy in substrate inspection device 201 of this embodiment.

Moreover, the distribution of defects on sample substrate 202 can also be effectively detected because the scattering matrix for a case in which a pair of standard substrates 203 are successively rotated a predetermined angle with respect to electrode member 204 is compared with the scattering matrix for a case in which each of substrates 202 and 203 are successively rotated the predetermined angle with respect to electrode member 204.

Further, the surfaces of each of substrates 202 and 203 are electrically charged by ionized air in substrate inspection device 201 of this embodiment, and if the defect on the surface of sample substrate 202 is adhered foreign matters, this foreign matters is charged depending on the polarity. In this case, the equation satisfied by the propagated RF electromagnetic waves is:

$$[(\partial^2/\partial x^2)+(\partial^2/\partial y^2)+k^2]EZ(x, y)=[j\omega/(\delta+j\epsilon\omega)]\rho(X', y') \quad (15)$$

The right side of this equation (15) indicates the charge distribution of the defect ρ(x', y'), and this reflects the scattering effect of RF electromagnetic waves. Using the solution to the abovementioned equation (12) as base, this equation (15) can be solved by a Green function, and the nature and distribution of the foreign matters can therefore be analyzed by comparing the theoretical value with the actually measured value of sample substrate 202.

For example, a known table generally referred to as "charging series" lists various substances in order of changes in charged state brought about by the introduction of ions, from a positive end to a negative end, such as "silicon elastomer with silica filler," "borosilicate glass, fire-polished," and so on to "polytetrafluoroethylene."

If the state of ionization of air supplied to the surfaces of each of substrates 202 and 203 is changed and the corresponding changes in measurement results by the network analyzer 205 are observed, changes in the charged state of the surface of sample substrate 202 can be detected and the composition of the foreign matters can be analyzed by referring to the above-described "charging series."

In the substrate analysis method by substrate inspection device 201 of this embodiment, the state of the surface of sample substrate 202 is inspected based on the propagation characteristics of RF electromagnetic waves of electrode member 204 as described hereinabove, and a device of large scale or complicated structure is therefore not required, and the operation does not require a great deal of time.

As a result, substrate inspection device 201 may be added as one part of a circuit fabrication line, a silicon wafer in the process of fabricating integrated circuits may be taken as sample substrate 202, and the surface state can be inspected quickly and automatically. Moreover, the measurement results for a pair of standard substrates 203 are registered beforehand and these are compared with the measurement results for sample substrate 202, whereby the presence of defects in the surface of sample substrate 202 can be determined easily and with good accuracy.

In addition, RF electromagnetic waves are uniformly applied to the even-numbered electrode wires of a multiplicity of electrode wires 211 arranged on electrode member 204 and the RF electromagnetic waves generated in the odd-numbered electrode wires 211 are detected for each of four divisions, whereby the distribution of defects in sample substrate 202 can be analyzed from a scattering matrix. The propagation characteristics of the RF electromagnetic waves are measured for each predetermined angle of rotation of each of substrates 202 and 203 relative to electrode member 204, whereby the distribution of defects of sample substrate 202 can be analyzed with still greater accuracy.

At this time, each of substrates 202 and 203 are axially supported by axial support structure 226 so as to confront electrode member 204 but remain out of contact with and separated by a predetermined distance from electrode member 204, and sample substrate 202 can therefore be easily rotated without being contaminated. In particular, defects on the surface of sample substrate 202 can be effectively detected even if integrated circuits in a stage of fabrication are formed on the surface because substrates 202 and 203 are rotated as a unit.

Further, foreign matters adhering to the surface of sample substrate 202 can be detected with good accuracy because the surfaces of each of substrates 202 and 203 that confront electrode member 204 are subjected to electrical charging. In particular, the surface of sample substrate 202 need not contact an electrode because the surfaces of each of substrates 202 and 203 are charged by supplying ionized air, and contamination of the surface of sample substrate 202 can therefore be prevented.

Each of substrates 202 and 203 are supported by axial support structure 226 so as to confront electrode member 204 but remain out of contact with and separated by a predetermined distance from electrode member 204 as described above, and ionized air can therefore be easily supplied to the surfaces of each of substrates 202 and 203 that confront electrode member 204.

In particular, a multiplicity of electrode wires 211 are arranged in the same direction on electrode member 204 and ionized air is supplied to the gaps between these electrode wires 211, and ionized air can therefore be easily and reliably supplied to the minute space between the surfaces of substrates 202 and 203.

Moreover, the state of ionization of air supplied to the surfaces of substrates 202 and 203 is changed, and the composition of foreign matters present on the surface of sample substrate 202 is analyzed based on the measurement results corresponding to these changes, thereby enabling easy analysis by means of a simple construction of the composition of foreign matters present on the surface of sample substrate 202.

In addition, the atmosphere in which each of substrates 202 and 203 and electrode member 204 are situated is kept in a dry state by dry box 222, thereby preventing natural discharge on the surface of sample substrate 202, enabling effective maintenance of the charged state, and enabling highly accurate detection of the distribution of defects and analysis of composition based on electrical charge.

Further, each of substrates 202 and 203 and electrode member 204 are enclosed within shield box 221, thereby preventing intrusion of electromagnetic waves from the outside as noise to electrode member 204 that propagates RF electromagnetic waves, and analysis of the presence, distribution, and composition of defects on sample substrate 202 can be carried out with good accuracy.

In particular, dry box 222 is provided on the bottom of shield box 221 as a unit, and the positions of each of substrates 202 and 203 and electrode member 204 can therefore be kept both shielded and dry, and since only a single housing is required, the overall construction can be made lighter and more compact.

In addition, sample substrate 202 is typically conveyed with the surface on which integrated circuits are formed as the upper surface, and in substrate inspection device 201 of this embodiment, the tested surface of sample substrate 202 is oriented up, whereby sample substrate 202 conveyed on the circuit fabrication line can be conveyed into the inspection device and inspected without turning sample substrate 202 over.

In the above-described embodiment, an example was described in which electrode member 204 is provided with four input terminals 213–216 to which RF electromagnetic waves are supplied, but the number of input terminals can be freely set.

Increasing the number of input terminals 213- of electrode member 204 makes the construction of electrode member 204 more complex and complicates the wiring with network analyzer 205 but improves the resolution of detecting the distribution of defects. On the other hand, decreasing the number of input terminals 213- of electrode member 204 reduces the resolution of detecting the distribution of defects but simplifies the construction of electrode member 204 and simplifies the wiring with network analyzer 205. The number of input terminals 213- of electrode member 204 should therefore be determined with due consideration given to various conditions such as the specifications of substrate inspection device 201.

Similarly, an example was described in the abovementioned embodiment in which each of substrates 202 and 203 are rotated as much as 90° a single time with respect to electrode member 204. Decreasing the degrees of rotation and increasing the number of instances of rotation, while lengthening the process, affords an improvement in the resolution of detecting the distribution of defects. Nevertheless, if a multiplicity of electrode wires 211 is arranged in parallel in electrode member 204 as described hereinabove, rotating each of substrates 202 and 203 as much as 90° a single time allows the distribution of defects to be detected with high efficiency and good accuracy.

In addition, an example was described in the above-described embodiment in which each of substrates 202 and 203 are rotated as a unit with electrode member 204 fixed and immobile, but substrates 202 and 203 may be supported in a fixed position and electrode member 204 rotated, or both of substrates 202 and 203 and electrode member 204 may be rotated relative to each other. If substrates 202 and 203 are composed of disk silicon wafers as described above, however, supporting and rotating the wafers is relatively easy while rotating electrode member 204, which is wired to network analyzer 205, is difficult, and it is therefore suitable to keep electrode member 204 fixed while rotating substrates 202 and 203 as a unit as described above.

In the above-described embodiment, sample substrate 202 was assumed to be a silicon wafer in the process of having integrated circuits formed, but various wafers may be taken as the subject of inspection in substrate inspection device 201 of this invention. As described above, when a silicon wafer undergoing the process of integrated circuit formation is taken as sample substrate 202, the surface of the wafer is not uniform even if no defects are present.

Therefore, when registering measurement results for a pair of standard substrates 203 in a data storage means under the setting of the data registering mode in a case in which wafers are rotated to detect the distribution of defects on the abovementioned sample substrate 202, the pair of standard substrates 203 are preferably rotated with respect to electrode member 204 and the measurement results registered together with identifier data for the angle of rotation.

An isotropic sample substrate not having integrated circuits formed on the surface that is taken as the subject of inspection, however, has a uniform surface state assuming no defects are present. In such a case, therefore, the pair of standard substrates is not rotated with respect to the electrode member when registering measurement results in the data storage means, and the sample substrate need only be rotated only when measuring the characteristics from the sample substrate under the setting of inspecting mode.

The measurement results by network analyzer 205 may be registered directly for the measurement results of the pair of standard substrates 203 stored in the data storage means as described above, but when making the final calculation of the scattering matrix and comparing as described above, the scattering matrix may be calculated and registered in advance without direct measurement.

In the above-described embodiment, an example was described in which RF electromagnetic waves are first supplied simultaneously and uniformly to the plurality of input terminals 213–216 of electrode member 204 to inspect all regions of the surface of sample substrate 202, and if the presence of defects is thereupon confirmed, RF electromagnetic waves are then supplied in order to the plurality of input terminals 213–216 to inspect in order portions of the surface of sample substrate 202. However, the surface of sample substrate 202 may also be inspected portion by portion from the beginning, and then giving sample substrate 202 a close inspection by a different method when inspection of all regions confirms the presence of defects. Similarly, although an example was described in the above embodiment in which substrates 202 and 203 were rotated to detect the distribution of defects and then the state of charging was varied to detect the composition of defects, these processes may be combined in any order.

While preferred embodiments according to the present invention have been described using specific terms, such description is for illustrative purposes only, and it is to be understood that changes and variations may be made without departing from the spirit or scope of the following claims.

What is claimed is:

1. A substrate inspection method, comprising the steps of:

preparing a standard substrate of good quality and of a structure symmetrical to that of a sample substrate to be inspected;

arranging a first electrode plate, said standard substrate, a second electrode plate, said sample substrate, and a third electrode plate, in that order, with the standard substrate and said sample substrate facing symmetrically with each other;

measuring, via a network analyzer, both the propagation characteristics of radio frequency (RF) electromagnetic waves from said second electrode plate to said first electrode plate as standard characteristics and the propagation characteristics of RF electromagnetic waves from said second electrode plate to said third electrode plate as test characteristics;

comparing the test characteristics with the measured standard characteristics to determine whether said sample substrate is good or bad; and preparing, as said second electrode plate, a component in which a central portion where said standard and sample substrate are to be arranged is formed in a reticulated form, and in which an outer edge is divided into a plurality of outer edge portions that are connected to said network analyzer; and wherein said step of measuring standard characteristics and test characteristics further includes the steps of:

applying RF electromagnetic waves to at least one of said plurality of outer edge portions of said second electrode plate by said network analyzer, and measuring RF electromagnetic waves generated at at least one of said outer edge portions.

2. The method of claim 1, wherein said step of measuring standard characteristics and test characteristics, comprises the steps of:
sequentially measuring, via said network analyzer, RF electromagnetic waves from one of said outer edge portions to another of said outer edge portions; and
analyzing a distribution of defects of said sample substrate as positions relative to said second electrode plate based on measurement results of said network analyzer.

3. The method of claim 2, wherein said step of sequentially measuring further comprises the step of rotating said standard substrate and said sample substrate relative to said second electrode plate.

4. The method of claim 1, wherein the following relations are satisfied:
$a \approx \lambda$
$d << \lambda$
where $\lambda$ is a wavelength of the RF electromagnetic waves generated by said network analyzer, d is a thickness of said sample substrate and said standard substrate, a is a diameter of said sample substrate and said standard substrate.

5. A substrate inspection device, comprising:
a standard substrate of good quality and of a structure symmetrical to that of a sample substrate to be inspected;
a first electrode plate arranged on an obverse surface of said standard substrate;
a second electrode plate arranged in a space between a reverse surface of said standard substrate and an obverse surface of said sample substrate;
a third electrode plate arranged on a reverse surface of said sample substrate;
a network analyzer for measuring propagation characteristics of radio frequency (RF) electromagnetic waves from said second electrode plate to said first electrode plate as standard characteristics and the propagation characteristics of RF electromagnetic waves from said second electrode plate to said third electrode plate as test characteristics; and
a quality judging means for comparing the test characteristics with the measured standard characteristics to determine whether said sample substrate is good or bad,
wherein a central portion of said second electrode plate where said standard substrate and said sample substrate are to be arranged is formed in a reticulated form, and
an outer edge portion of said second electrode plate to be connected to said network analyzer is divided into a plurality of portions.

6. The device of claim 5, wherein the following relations are satisfied:
$a \approx \lambda$
$d << \lambda$
where $\lambda$ is a wavelength of the RF electromagnetic waves generated by said network analyzer, d is a thickness of said sample substrate and said standard substrate, a is a diameter of said sample substrate and said standard substrate.

7. A substrate inspection method, comprising the steps of:
preparing a standard substrate of good quality and of a structure symmetrical to that of a sample substrate to be inspected;
arranging said standard substrate and said sample substrate in symmetrical opposition with a flat electrode member interposed therebetween;
causing radio frequency (RF) electromagnetic waves to propagate in said electrode member that confronts said standard substrate on its obverse side and said sample substrate on its reverse side and measuring characteristics of RF electromagnetic waves by a network analyzer;
determining whether or not defects exist on a surface of said sample substrate based on results of said characteristics; and
preparing, as said electrode member, a component having a multiplicity of linear electrode wires arranged in parallel with each other in a planer form,
wherein said step of propagating RF electromagnetic waves in said electrode member and measuring characteristics includes the steps of:
applying RF electromagnetic waves, via said network analyzer, to either odd-numbered or even-numbered electrode wires of said multiplicity of electrode wires; and
measuring RF electromagnetic waves generated in the other of either the odd-numbered electrode wires or even-numbered electrode wires of said multiplicity of electrode wires.

8. The method of claim 7, further comprising the step of:
storing measurement results, via said network analyzer, using another standard substrate in place of said sample substrate,
wherein said step of determining whether or not defects exist on the surface of said sample substrate includes the step of comparing the measurement results of said sample substrate with the stored measurement results.

9. The method of claim 7, further comprising the step of:
dividing said multiplicity of electrode wires into a plurality of sectors,
wherein said step of propagating RF electromagnetic waves in said electrode member and measuring characteristics includes the step of sequentially applying, for each of the plurality of sectors, RF electromagnetic waves to said multiplicity of electrode wires via said network analyzer.

10. The method of claim 9, further comprising a step of:
analyzing a distribution of defects of said sample substrate including generating a scattering matrix based on a plurality of measurement results of RF electromagnetic waves sequentially detected by said network analyzer.

11. The method of claim 10, wherein said step of arranging said standard substrate and said sample substrate includes the step of:
placing said standard substrate and said sample substrate in opposition to said electrode member but out of contact with said electrode member and separated from said electrode member by a predetermined distance, and
said step of analyzing the distribution of defects includes steps of:
rotating said standard substrate and said sample substrate relative to said electrode member; and
analyzing the distribution of defects of said sample substrate based on a plurality of measurement results made via said network analyzer and corresponding to said rotation.

12. The method of claim 7, further comprising the step of charging surfaces of said sample substrate and said standard substrate that face said electrode member.

13. The method of claim 12, further comprising the step of supplying ionized air to said surfaces of said sample substrate and said standard substrate that face said electrode member.

14. The method of claim 13, wherein said step of supplying ionized air to the surfaces includes the step of varying a state of ionization of air supplied to the surfaces, and said step of determining whether or not defects exist on the surface of said sample substrate includes the step of analyzing a composition of foreign matter existing on the surface of said sample substrate based on changes in the measurement results via said network analyzer corresponding to the state of ionization of the supplied air.

15. The method of claim 13, wherein said step of supplying ionized air to the surfaces includes the step of supplying ionized air to gaps between said multiplicity of electrode wires of said electrode member.

16. The method of claim 15, wherein said step of supplying ionized air to the surfaces includes the step of varying a state of ionization of air supplied to the surfaces, and said step of determining whether or not defects exist on the surface of said sample substrate includes the step of analyzing a composition of foreign matter existing on the surface of said sample substrate based on changes in the measurement results via said network analyzer corresponding to the state of ionization of the supplied air.

17. The method of claim 12, further comprising the step of maintaining the atmosphere at least where said standard substrate and said sample substrate are located in a dry state.

18. The method of claim 7, further comprising the step of preventing intrusion of electromagnetic waves from outside into said standard substrate and said sample substrate.

19. A substrate inspection method, comprising the steps of:

preparing a standard substrate of good quality and of a structure symmetrical to that of a sample substrate to be inspected;

arranging a first electrode plate, said standard substrate, a second electrode plate, said sample substrate, and a third electrode plate, in that order, with the standard substrate and said sample substrate facing symmetrically with each other;

measuring, via a network analyzer, both the propagation characteristics of radio frequency (RF) electromagnetic waves from said second electrode plate to said first electrode plate as standard characteristics and the propagation characteristics of RF electromagnetic waves from said second electrode plate to said third electrode plate as test characteristics; and comparing the test characteristics with the measured standard characteristics to determine whether said sample substrate is good or bad.

20. A substrate inspection device, comprising:

a standard substrate of good quality and of a structure symmetrical to that of a sample substrate to be inspected;

a first electrode plate arranged on an obverse surface of said standard substrate;

a second electrode plate arranged in a space between a reverse surface of said standard substrate and an obverse surface of said sample substrate;

a third electrode plate arranged on a reverse surface of said sample substrate;

a network analyzer for measuring propagation characteristics of radio frequency (RF) electromagnetic waves from said second electrode plate to said first electrode plate as standard characteristics and the propagation characteristics of RF electromagnetic waves from said second electrode plate to said third electrode plate as test characteristics; and a quality judging means for comparing the test characteristics with the measured standard characteristics to determine whether said sample substrate is good or bad.

21. A substrate inspection method, comprising the steps of:

preparing a standard substrate of good quality and of a structure symmetrical to that of a sample substrate to be inspected;

arranging said standard substrate and said sample substrate in symmetrical opposition with a flat electrode member interposed therebetween;

causing radio frequency (RF) electromagnetic waves to propagate in said electrode member that confronts said standard substrate on its obverse side and said sample substrate on its reverse side;

separately receiving RF electromagnetic waves propagated from the electrode member through the standard substrate on a side thereof opposite to the obverse side and through the sample substrate on a side thereof opposite to the reverse side;

measuring characteristics of the separately received RF electromagnetic waves; and determining whether or not defects exist on a surface of said sample substrate based on the results of said measuring step.

* * * * *